United States Patent
Nielsen et al.

(10) Patent No.: US 8,201,557 B2
(45) Date of Patent: Jun. 19, 2012

(54) METHOD TO COMPENSATE FOR THE EFFECT OF RECIRCULATION OF INERT BLOOD SOLUBLE GAS ON THE DETERMINATION OF PULMONARY BLOOD FLOW IN REPEATED INERT GAS REBREATHING TESTS

(75) Inventors: Jørgen Grønlund Nielsen, Glamsbjerg (DK); Peter Christian Clemensen, Odense C (DK)

(73) Assignee: Innovision A/S, Odense S (DK)

( * ) Notice: Subject to any disclaimer, the term of this patent is extended or adjusted under 35 U.S.C. 154(b) by 664 days.

(21) Appl. No.: 12/309,934

(22) PCT Filed: Aug. 3, 2007

(86) PCT No.: PCT/DK2007/000367
§ 371 (c)(1), (2), (4) Date: Mar. 30, 2009

(87) PCT Pub. No.: WO2008/014788
PCT Pub. Date: Feb. 7, 2008

(65) Prior Publication Data
US 2009/0320844 A1    Dec. 31, 2009

(30) Foreign Application Priority Data
Aug. 4, 2006  (DK) .................................. 2006 01035

(51) Int. Cl.
*A62B 7/00*    (2006.01)

(52) U.S. Cl. .................................. 128/204.22; 600/532
(58) Field of Classification Search .................. 600/532; 128/204.22
See application file for complete search history.

(56) References Cited

U.S. PATENT DOCUMENTS 3,613,665 A * 10/1971 Gorsuch ........................ 600/543
3,661,528 A *  5/1972 Falk ............................. 73/863.01
3,910,261 A * 10/1975 Ragsdale et al. .............. 600/532
(Continued)

FOREIGN PATENT DOCUMENTS
WO    WO 00/13579      3/2000
WO    WO 2006/119546  11/2006

OTHER PUBLICATIONS

Becklake et al., "Measurement of pulmonary blood flow during exercise using nitrous oxide", Journal of applied physiology (0021-8987), Jul. 1962 vol. 17;p. 579-86.*

(Continued)

*Primary Examiner* — Samuel G. Gilbert
*Assistant Examiner* — Sunita Reddy
(74) *Attorney, Agent, or Firm* — Day Pitney LLP

(57) ABSTRACT

The present invention discloses a method to compensate for a non-zero mixed venous partial pressure of inert blood soluble gas when determining physical parameter(s) of a patient in successive inert gas rebreathing tests. The method comprises the steps of: obtaining the partial pressure of said inert blood soluble gas inhaled and/or exhaled by said patient in a period prior to said successive rebreathing test; obtaining the partial pressure of said inert blood soluble gas inhaled and/or exhaled by said patient in said successive rebreathing test; determining said physical parameters) using said partial pressure of said inert blood soluble gas inhaled and/or exhaled by said patient and obtained in said period prior to said successive rebreathing test and said partial pressure of said inert blood soluble gas inhaled and/or exhaled by said patient and obtained in said successive rebreathing test. Furthermore the present invention relates to a corresponding system and computer-readable medium.

19 Claims, 5 Drawing Sheets

U.S. PATENT DOCUMENTS

| | | | | |
|---|---|---|---|---|
| 4,062,373 | A | * | 12/1977 | Clark et al. .................. 137/3 |
| 4,221,224 | A | * | 9/1980 | Clark ........................... 600/531 |
| 4,440,177 | A | * | 4/1984 | Anderson et al. ............. 600/532 |
| 4,941,476 | A | * | 7/1990 | Fisher .......................... 600/532 |
| 5,540,233 | A | * | 7/1996 | Larsson et al. ............... 600/538 |
| 5,971,934 | A | * | 10/1999 | Scherer et al. ............... 600/526 |
| 6,402,697 | B1 | * | 6/2002 | Calkins et al. ............... 600/532 |
| 6,622,725 | B1 | * | 9/2003 | Fisher et al. ............. 128/204.21 |
| 2003/0040678 | A1 | * | 2/2003 | Robinson ..................... 600/531 |
| 2004/0028753 | A1 | * | 2/2004 | Hedenstierna et al. ....... 424/718 |

OTHER PUBLICATIONS

"Validation of the acetylene rebreathing method for measurement of cardiac output at rest and during high-intensity exercise", Liu, Y et al.Clinical Physiology , 1997, 17, 171-182 (XP-002476665).

"The effect of incomplete acetylene washout on cardiac output measurement using open circuit acetylene uptake", Balouch, Jamal, Science Direct, Respiratory Physiology & Neurobiology 155 (2007) 177-183.

Balouch et al.: "The effect of incomplete acetylene washout on cardiac output measurement using open circuit acetylene uptake", May 22, 2006, Respiratory Physiology and Neurobiology, Elsevier, Amsterdam, NL pp. 177-183, XP005857814 ISSN: 156909048, p. 178, col. 1, line 40-p. 179, col. 2, line 36.

Liu Y et al: "Validation of the acetylene rebreathing method for measurement of cardiac output at rest and during high-intensity exercise", Mar. 1997, Clinical Physiology (Oxford, England) vol. 17, NR. 2, pp. 171-182, XP002476665 ISSN: 0144-5979.

* cited by examiner

METHOD TO COMPENSATE FOR THE EFFECT OF RECIRCULATION OF INERT BLOOD SOLUBLE GAS ON THE DETERMINATION OF PULMONARY BLOOD FLOW IN REPEATED INERT GAS REBREATHING TESTS

FIELD OF THE INVENTION

The present invention relates to a method to compensate for the effect of recirculation of inert blood soluble gas on the determination of pulmonary blood flow or cardiac output in repeated inert gas rebreathing tests.

BACKGROUND

One way of examining the function and performance of a patient's heart is by determining the cardiac output, i.e. the amount of blood pumped by the left ventricle per unit time. A well-established method to measure the cardiac output is by inert gas rebreathing, which is a non-invasive measurement method to determine pulmonary blood flow. The pulmonary blood flow is equal to the cardiac output in the absence of a significant intrapulmonary shunt.

The method uses a mixture containing two inert gases, a blood soluble and a blood insoluble compound. The blood soluble gas and preferably also the insoluble gas are not present in ambient or normal expired air. Blood soluble gases that can be used in inert gas rebreathing tests are e.g. nitrous oxide, acetylene and chlorodifluoromethane (Freon 22). The principle of the method is to have the patient inhale the gas mixture from a rebreathing bag and breathe the gas mixture in a closed rebreathing assembly for a short period of time (e.g. 10-15 seconds) (here and in the following called a rebreathing test or rebreathing period). When the blood soluble compound comes in contact with the blood perfusing the lungs it is absorbed and therefore gradually disappears from the rebreathing assembly. The faster the blood flows, the quicker the blood soluble gas disappears.

The blood insoluble compound is used to determine the lung volume, which is an important variable in the relationship between the disappearance rate of the blood soluble gas and pulmonary blood flow. It is also used as a tracer substance to account for various basic assumptions of the underlying lung model. Thus, the measurement of cardiac output or pulmonary blood flow is a matter of measuring the rate of disappearance of blood soluble gas from the rebreathing system and the dilution of insoluble gas.

Non-invasive measurement of cardiac output or pulmonary blood flow by inert gas rebreathing is important in a variety of clinical settings where invasive methods should be avoided or where other non-invasive methods are e.g. either unreliable or impractical.

One of the main assumptions of the inert gas rebreathing method to measure pulmonary blood flow is that the partial pressure of the inert blood soluble compound in the mixed venous blood is zero during the test.

This assumption is correct when a patient is doing the first test in a series of tests. However, if subsequent tests are done with only a short time period between tests the assumption becomes invalid. This is because a small amount of the blood soluble gas is absorbed by the blood perfusing the lungs during a test and subsequently deposited in various tissues in the body. Between the tests (called a washout period) the deposited gas however diffuses back into the blood and is carried to the lungs in the mixed venous blood. Thus the partial pressure of the soluble gas in the mixed venous blood is no longer zero as assumed in the model. This situation is referred to as recirculation.

In order to avoid this problem the patient must be allowed enough time between two tests for the blood soluble gas to be washed out. This can be obtained with a break of around 5-10 minutes if the patient is relaxing or approximately 2-5 minutes during exercise. This obviously results in dramatically prolonged duration of the testing time needed for each patient and also adds considerably to the overall cost of performing the test. Furthermore, simply prolonging the tests in order to ensure that all the blood soluble gas is washed out is also not optimal in the case of the tests being performed while the patient is exercising. Here, a significant prolongation of the test would eventually lead to the patient getting exhausted too early which is undesirable. Also, in several clinical applications it is essential to do frequent measurements of the pulmonary blood flow in order to see and measure the immediate effect of different interventions such as adjustments of a biventricular pacemaker etc. In these cases the measured pulmonary blood flow hence becomes inaccurate as the aforementioned assumption of zero partial pressure of the blood soluble compound in mixed venous blood may no longer be valid.

Whether the mixed venous partial pressure of the blood soluble gas is non-zero can be seen in the expired air (end-tidal partial pressure of the gas) prior to the start of the rebreathing test provided that the gas analyzer is sufficiently sensitive to detect the trace amount of the blood soluble gas. However, the size of the mixed venous partial pressure of the blood soluble gas can not be measured directly by noninvasive means and even if it could the parameter is not used in the methods to determine the pulmonary blood flow as of the state of art.

Simulations have shown that the error on the measured blood flow can be quite significant if the mixed venous blood content is non-zero. The error is almost proportional to the ratio between the steady-state end-tidal level of blood soluble gas prior to rebreathing and the initial content in the rebreathing bag so that for each percent of this ratio the error (underestimation) is approximately 10% (simulation done with a resting blood flow of 5 l/min, a lung volume equal to the bag volume of 2 l, and an alveolar ventilation of 7 l/min). If a test is repeated after e.g. 30 seconds the error can easily be in the order of 30%. This again leads to an unacceptable uncertainty in the diagnosis or treatment of the patient.

The problem of recirculation is seldom considered in the known art. In U.S. Pat. No. 4,363,327 the pulmonary blood flow is determined based on a number of repeated washin and washout periods. According to the document a cyclical injection of the blood soluble and insoluble inert gases is causing a cyclic steady-state whereby the changes in the venous concentrations of the soluble gas over a cycle period become small. The method is indifferent to unknown but slowly varying concentrations of soluble gases in the venous system, and the pulmonary blood flow is determined based on this observation. However, in order to realize this steady-state the method necessitates a rather large number of near-identical cycles (up to 30) to be performed before giving reliable results and further does not deal with how to compensate for incomplete washout of blood soluble gas in between measurements but rather describes a method which produces a significant venous return of the soluble gas.

In the paper by Balouch et al. ("The effect of incomplete acetylene washout on cardiac output measurement using open circuit acetylene uptake", Respir. Physiol. Neurobiol., 2006 May 19) the effect of incomplete acetylene washout on cardiac output measurement is considered during open circuit acetylene uptake. The calculation of the cardiac output is here determined by applying a correction factor estimating the mixed venous acetylene concentration from end-tidal values. As such the paper deals with the same basic problem of incomplete washout of blood soluble gas in between measurements of cardiac output. However, the method is applicable to open circuit acetylene uptake and can not readily be applied to the inert gas rebreathing method from which it differs in several ways. First, the open circuit method uses washin of a gas mixture through a one-way valve whereas the rebreathing method uses a closed system. Second, the method is more sensitive to inhomogeneities in the lungs because rebreathing is a more effective maneuver to obtain good mixing of the gases. Third, the washin period of the blood soluble gas is much longer than the rebreathing period and furthermore, the washin requires much more inert gas than rebreathing which makes the equipment more bulky and the procedure more expensive.

OBJECT AND SUMMARY OF THE INVENTION

The object of the present invention is therefore to provide a method to avoid some or all of the above mentioned problems in the determination of the pulmonary blood flow from use of the inert gas rebreathing method.

According to one aspect the present invention relates to a method to compensate for a non-zero mixed venous partial pressure of inert blood soluble gas when determining physical parameter(s) of a patient in successive inert gas rebreathing tests. The method comprises the steps of: obtaining the partial pressure of said inert blood soluble gas inhaled and/or exhaled by said patient in a period prior to said successive rebreathing test; obtaining the partial pressure of said inert blood soluble gas inhaled and/or exhaled by said patient in said successive rebreathing test; determining said physical parameter(s) using said partial pressure of said inert blood soluble gas inhaled and/or exhaled by said patient and obtained in said period prior to said successive rebreathing test and said partial pressure of said inert blood soluble gas inhaled and/or exhaled by said patient and obtained in said successive rebreathing test. The consequence is that the mixed venous partial pressure of inert blood soluble gas can be determined by using the obtained partial pressures of the inert blood soluble gas prior to and under the rebreathing test and the mathematical methods disclosed in this application. The advantage is that the washout period between two successive rebreathing tests can be shortened compared to the prior art techniques. The result is that the physical parameter(s) of the patient could be determined much faster. Further the physical parameter(s) could be determined much more precisely due to the fact that the mixed venous partial pressure of inert blood soluble gas is taken into account when determining the physical parameter(s). Thus, it is much easier for a clinician to perform the rebreathing tests. The partial pressure could for instance be obtained by using gas analyzers that can measure the partial pressure of the gas or can measure the concentration of the gas. A person skilled in the art would recognize that the partial pressure could be derived from the concentration and vice versa.

In one embodiment of the method, the step of determining said physical parameter(s) comprises the steps of: extracting a first parameter using said obtained partial pressure of said inert blood soluble gas inhaled and/or exhaled by said patient in said successive rebreathing test; extracting a second parameter using said first parameter and said obtained partial pressure of said inert blood soluble gas inhaled and/or exhaled by said patient in said period prior to said successive rebreathing test; re-extracting said first parameter using said second parameter and said obtained partial pressure of said inert blood soluble gas inhaled and/or exhaled by said patient in said successive rebreathing test and determining said physical parameter(s) using said first parameter, said second parameter and/or said re-extracted said first parameter. Hereby the physical parameter(s) could be determined by using an iterative process where a first parameter is re-extracted using a second parameter in order to compensate for the second parameter. The advantage is that the physical parameter(s) could be determined more accurately. The first and second parameters could be any kind of parameter extracted from the obtained partial pressure of the inert blood soluble gas such as values describing physical parameters of the patient and/or values derived from the physical parameters.

In another embodiment the method further comprises the step of: repeating the steps of extracting said second parameter and re-extracting said first parameter a number of times, such that said re-extracted first parameter is used in said step of extracting said second parameter. Hereby it is achieved that the iterative process described above could be repeated a number of times and/or until the parameters converge. The advantage is that the physical parameter(s) could be determined more accurately.

In another embodiment of the method, the steps of obtaining the partial pressure of said inert blood soluble gas comprises the step of obtaining the concentrations of said inert blood soluble gas. Hereby it is achieved that the partial pressure could be obtained by measuring the concentration of the inert blood soluble gas inhaled and/or exhaled by the patient and the partial pressure of the inert blood soluble gas could then be calculated.

In another embodiment of the method, the first parameter comprises a cardiac parameter comprising the cardiac output of said patient. Hereby it is achieved that the physical parameter(s) of the patient could be derived from the first parameter and used in the iterative process. The cardiac parameter could for instance be the pulmonary blood flow of the patient; the cardiac output of the patient; the cardiac index defining the cardiac output per body surface area of the patient; the stroke volume defining the cardiac output per heartbeat or other parameters derived from the cardiac output or pulmonary blood flow.

In another embodiment of the method, the second parameter comprises the mixed venous partial pressure of said inert blood soluble gas. The advantage is that the mixed venous partial pressure of said inert blood soluble gas would be comprised in the iterative process when determining the physical parameter(s) of the patient. It is therefore possible to compensate for the mixed venous partial pressure of said inert blood soluble gas when determining the physical parameter(s) of the patient.

In another embodiment the method further comprises the steps of: obtaining the partial pressure of an inert blood insoluble gas inhaled and/or exhaled by said patient; and the step of using said partial pressure of said inert blood insoluble gas when determining said physical parameter(s), said first parameter, and/or said second parameter. Hereby it is achieved that the partial pressure of an inert blood insoluble gas could be used when determining the physical parameter(s) of the patient. The advantages of this are that the lung volume can be determined during the same test and that it is possible to account for various basic assumptions of the underlying lung model (e.g. incomplete mixing). The partial pressure of the inert blood insoluble gas could be obtained by using a gas analyzer that can measure the partial pressure of the gas or can measure the concentration of the gas. A person skilled in the art would recognize that the partial pressure could be derived from the concentration and vice versa.

In another embodiment of the method, the step of obtaining the partial pressure of said inert blood insoluble gas comprises the step of obtaining the concentration of said inert blood insoluble gas. Hereby it is achieved that the partial pressure could be obtained by measuring the concentration of the inert blood insoluble gas inhaled and/or exhaled by the patient and the partial pressure of the inert blood insoluble gas could then be calculated.

In another embodiment the method further comprises the step of obtaining the gas flow inhaled and/or exhaled by said patient. Hereby the gas flow inhaled and/or exhaled could be used when determining the physical parameter(s) of the patient and the result is that the physical parameter(s) could be determined more accurately. The gas flow could for instance be the volume flow measured in volume per unit of time, mass flow measured in mass per unit of time or mole flow measured in mol per unit of time.

In another embodiment of the method, the step of determining said physical parameter(s) is based on mass conservation of said inert blood soluble gas and/or said inert blood insoluble gas. Hereby it is achieved that the physical parameter(s) could be determined using mass conservation of said inert blood soluble gas and/or said inert blood insoluble gas. The advantage is that very precise equations/models based on mass conservation could be used when determining the physical parameter(s) of the patient.

According to a second aspect the present invention also relates to a system adapted to compensate for a non-zero mixed venous partial pressure of inert blood soluble gas when determining physical parameter(s) of a patient in successive inert gas rebreathing tests, said system comprising: at least one gas analyzer for obtaining the partial pressure of said inert blood soluble gas inhaled and/or exhaled by said patient in a period prior to said successive rebreathing test; at least one gas analyzer for obtaining the partial pressure of said inert blood soluble gas inhaled and/or exhaled by said patient in said successive rebreathing test; processing means for determining said physical parameter(s) using said partial pressure of said inert blood soluble gas inhaled and/or exhaled by said patient and obtained in said period prior to said successive rebreathing test and said partial pressure of said inert blood soluble gas inhaled and/or exhaled by said patient and obtained in said successive rebreathing test. Hereby it is achieved that a system adapted to compensate for the non-zero mixed venous partial pressure of inert blood soluble gas in a rebreathing test could be constructed and thereby the same advantages as described above are achieved. The gas analyzers could be any apparatus suitable for obtaining said partial pressure of said inert blood soluble gas for instance by measuring the partial pressure or the concentration of the soluble gas. Such apparatus could for instance be an infrared photoacoustic multi-gas analyzer, a mass spectrometer etc.

In one embodiment of the system, said means for determining said physical parameter(s) comprises: processing means for extracting a first parameter using said obtained partial pressure of said inert blood soluble gas inhaled and/or exhaled by said patient in said successive rebreathing test; processing means for extracting a second parameter using said first parameter and said obtained partial pressure of said inert blood soluble gas inhaled and/or exhaled by said patient in said period prior to said successive rebreathing test; processing means for re-extracting said first parameter using said second parameter and said obtained partial pressure of said inert blood soluble gas inhaled and/or exhaled by said patient in said successive rebreathing test; and processing means for determining said physical parameter(s) using said first parameter, said second parameter and/or said re-extracted said first parameter. Hereby the same advantages as described above are achieved.

In another embodiment the system further comprises: processing means for repeating the steps of extracting said second parameter and re-extracting said first parameter a number of times, such that said re-extracted first parameter is used in said step of extracting said second parameter. Hereby the same advantages as described above are achieved.

In another embodiment of the system, the gas analyzers for obtaining the partial pressure of said inert blood soluble gas comprises means for obtaining the concentrations of said inert blood soluble gas. Hereby the same advantages as described above are achieved.

In another embodiment of the system, said first parameter comprises a cardiac parameter comprising the cardiac output of said patient. Hereby the same advantages as described above are achieved.

In another embodiment of the system, said second parameter comprises the mixed venous partial pressure of said inert blood soluble gas. Hereby the same advantages as described above are achieved.

In another embodiment the system further comprises: at least one gas analyzer for obtaining the mixed venous partial pressure of an inert blood insoluble gas inhaled and/or exhaled by said patient and processing means for using said partial pressure of said inert blood insoluble gas. Hereby the same advantages as described above are achieved.

In another embodiment of the system, said at least one gas analyzer for obtaining the partial pressure of an inert blood insoluble gas comprises means for obtaining the concentrations of said inert blood insoluble gas. Hereby the same advantages as described above are achieved.

In another embodiment the system further comprises a flowmeter for obtaining the gas flow inhaled and/or exhaled by said patient. Hereby the same advantages as described above are achieved.

In another embodiment of the system, said processing means for determining said physical parameter(s) uses mass conservation of said inert blood soluble gas and/or said inert blood insoluble gas. Hereby the same advantages as described above are achieved.

According to another aspect the present invention relates to a computer-readable medium having stored therein instructions for causing a processing unit to execute the above described method. Hereby the same advantages as described above are achieved.

BRIEF DESCRIPTION OF THE DRAWINGS

In the following, preferred embodiments of the invention will be described referring to the figures, where.

DESCRIPTION OF PREFERRED EMBODIMENTS

Figure 1:
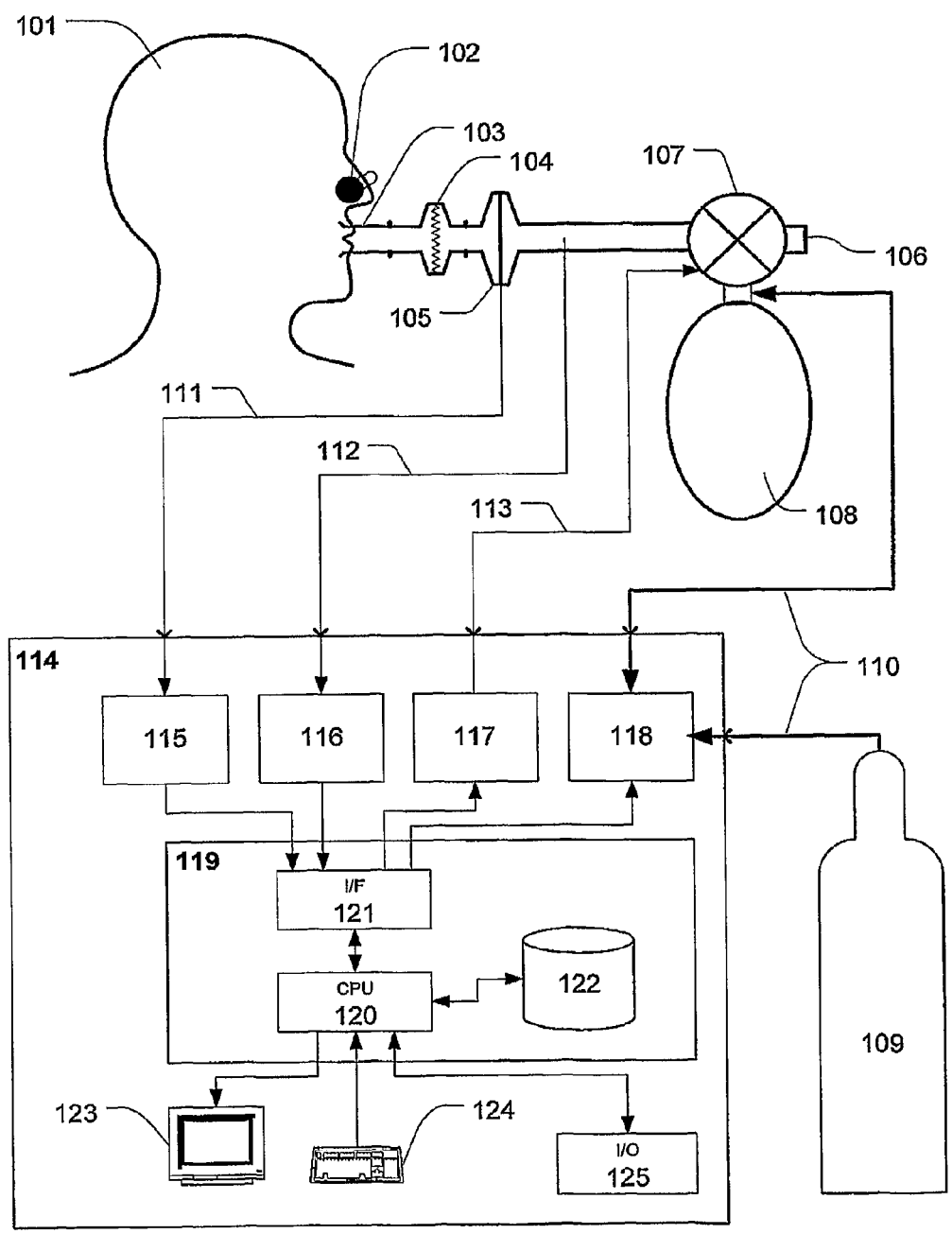
FIG. 1 is a schematic diagram illustrating a rebreathing apparatus and a system used in conjunction with the disclosed invention.

FIG. 1 illustrates a setup with a person or patient connected to a measuring apparatus performing a rebreathing test. A patient 101 having the nose occluded with a nose clip 102 breathes through a mouthpiece 103, a bacterial filter 104, a respiratory flowmeter 105 and one port 106 of a rebreathing valve assembly 107. A rebreathing bag 108 is connected to the valve assembly and evacuated and pre-filled with a gas mixture from a gas reservoir 109 via a gas line 110. Flowmeter connection(s) 111 and one or more gas sample lines 112 are also part of the setup.

To perform a rebreathing test the valve assembly 107 is switched (e.g. automatically by controlling line 113) to allow the patient 101 to inspire and rebreathe to and from the bag 108 for a certain amount of time until the valve assembly 107 is switched back again. The patient 101 may use a face mask instead of nose clip 102 and mouthpiece 103. The control system 114 of the measuring apparatus consists of flowmeter electronics 115, at least one or two gas analyzers 116, a valve control unit 117 (unless the valve assembly is manually driven), and a gas control unit 118 (unless the bag is prepared manually). A control unit 119 is also included, comprising a computing/processing unit (CPU) 120 with control interfaces 121, one or more program and data storage devices 122 and user interfaces for example comprising a display 123 and a keyboard, touch screen or similar input device 124. A data input/output module 125 may also be included.

Prior to the rebreathing tests the rebreathing bag is filled with a known volume of an inert gas mixture. During the testing the patient is breathing through the respiration valve, which allows switching from breathing air to rebreathing the inert gas mixture from the bag and switching back again.

A typical test may consist of a number of periods where the patient is breathing to and from the bag (rebreathing periods) alternating with periods where the patient is breathing fresh air (washout periods). During the testing (during both the rebreathing and the washout periods) the concentrations in the inhaled and/or exhaled air of the different inert gases in the mixture are measured by one or more fast responding gas analyzers 116. Hereby the concentration curves as illustrated later in FIGS. 3 and 5 can be obtained. Instead of gas concentrations the gas analyzers may equally well measure the partial pressures of the gases. Partial pressures can be obtained from fractional concentrations of dry gas or any other measure of gas concentration or pressure using appropriate conversion factors as known in the art. Also the flow of the inhaled and/or exhaled air is measured by means of the flowmeter 115. Alternatively a spirometer or similar volume measuring instrument can be used. These measurements can be made continuously or e.g. for each breath.

After a traditional rebreathing test where measurements are made of the gas flows and concentrations as described above, the rebreathing period is then followed by a washout period during which any measurements are not necessarily made as these data are traditionally not really used for the determination of the physiological parameters. In the present invention this is however not the case. Instead, according to one embodiment of the invention, the test data from one washout period is used in conjunction with the data from a subsequent rebreathing test to obtain the desired physiological parameters such as the pulmonary blood flow. In this way the data from the rebreathing period are in a sense corrected for the different starting or, boundary conditions arising from the patient having already breathed the gas mixture in a previous rebreathing period. By this method according to the invention it is possible to account for a non-zero partial pressure of the blood soluble gas in the mixed venous blood and even to determine the size of this as well. This will be demonstrated in the following.

Figure 2:
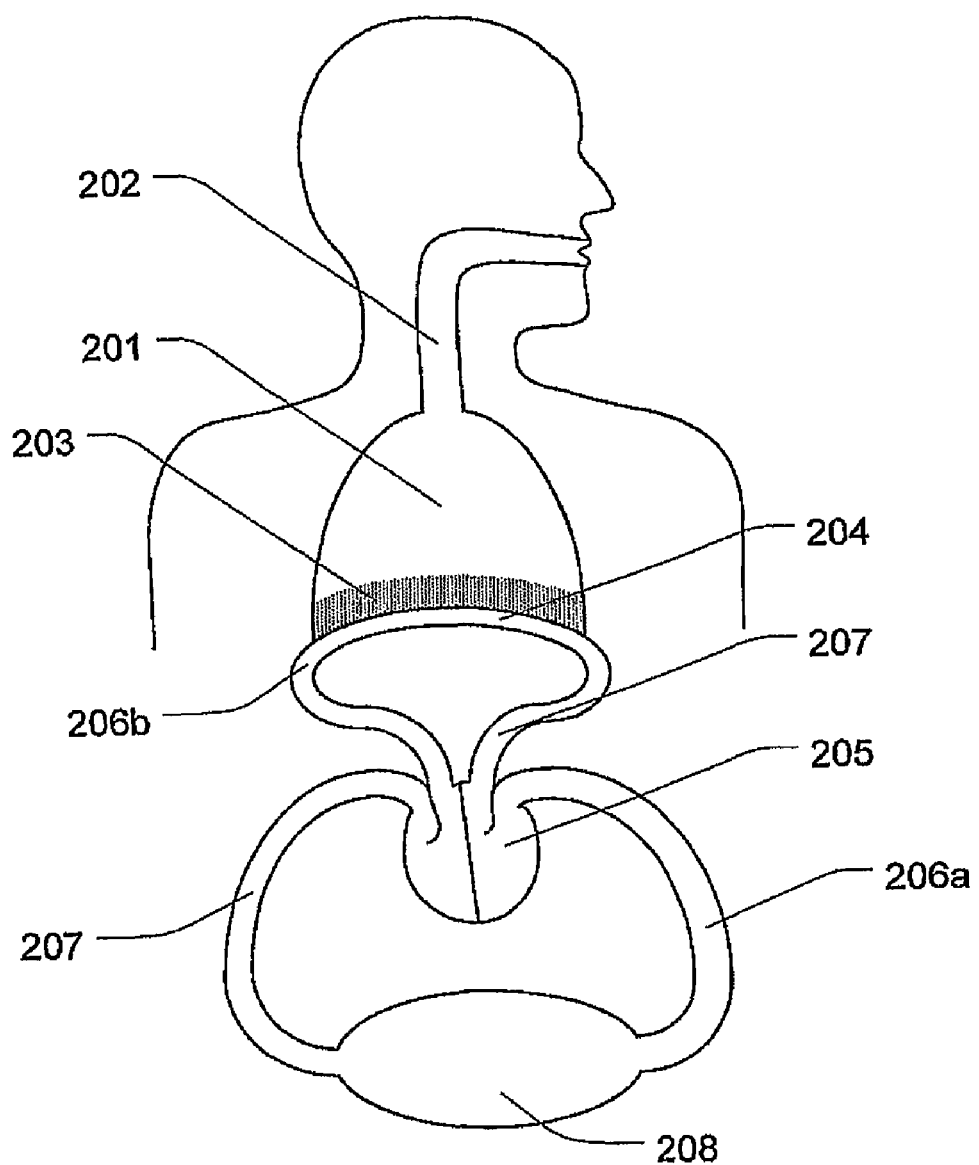
FIG. 2 is a schematic diagram illustrating a simplified single-compartment lung model used in conjunction with the disclosed invention.

FIG. 2 is an illustration of a simplified single-compartment lung model which constitutes the basis of the determination of the different physiological parameters from a rebreathing test. The simplified lung model consists of a single lung compartment 201 which includes a serial dead space consisting of the upper airways 202. Gas exchange takes place between the lung compartment 201 and the lung tissue volume 203 and lung capillaries 204, respectively. The lung capillaries are part of the circulatory system consisting of the heart 205, arteries 206, veins 207 and tissues 208. Cardiac output is the amount of blood ejected from the heart into the aorta 206a per unit time. In the absence of an intrapulmonary shunt this is equal to the pulmonary blood flow ejected into the pulmonary artery 206b, which carries mixed venous blood.

The quantitative relationship between the disappearance rate of the blood soluble gas and the pulmonary blood flow is derived by an analysis of a simplified model of the lung, as illustrated in FIG. 2 assuming just one well mixed gas compartment. However, this simplified model does not completely reflect the behavior of the human lung, which typically acts more like a model with several compartments. In order to account for the deviation from the model, the inert gas rebreathing method is also using a blood insoluble compound. The rebreathing curve of this blood insoluble gas is used to correct or adjust the rebreathing curve of the blood soluble gas to obtain better agreement with the model assumptions. The insoluble gas is also used to determine the lung volume, which is an important variable in the relationship between the disappearance rate of the blood soluble gas and pulmonary blood flow.

Blood soluble gases that can be used in inert gas rebreathing tests are for example nitrous oxide, acetylene, and chlorodifluoromethane (freon 22). Examples of insoluble gases are sulphur hexafluoride, helium, methane, neon, and argon. They are all but argon foreign gases in the sense that they are not present in the natural environment.

Figure 3:
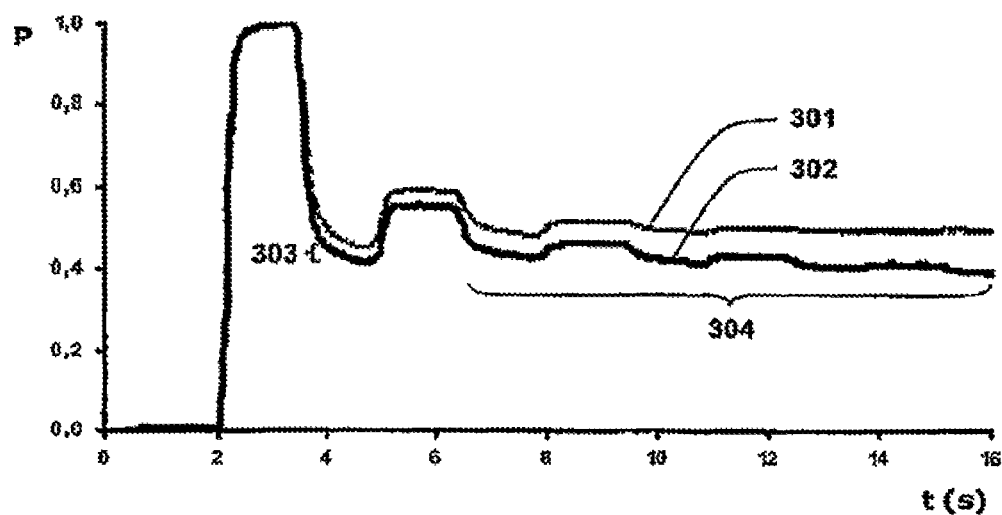
FIG. 3 is an example of blood soluble and insoluble gas rebreathing curves from a test as known in the art.

FIG. 3 illustrates representative curves of an insoluble 301 and a blood soluble 302 gas from a rebreathing test as known in the art. The curves are here scaled to a maximum of 1 during the first inspiration.

According to the single-compartment model of the lungs (FIG. 2) during rebreathing the partial pressure of the blood insoluble gas will equilibrate rapidly at a level determined by the ratio of the rebreathing bag volume and the combined bag and lung volume as can be seen from FIG. 3. At the same time an amount of the blood soluble gas disappears from the lungs due to dissolution in lung tissue and blood (FIG. 3). An initial nearly instantaneous disappearance of blood soluble gas 303 is ascribed to dissolution of the gas in lung tissue, while the later gradual decrease 304 is due to washout into the blood perfusing the lungs. The disappearance curve of the blood soluble gas describes a mono-exponentially decreasing curve as a function of time, since the rate of absorption is also proportional to the partial pressure of the blood soluble gas. As mentioned above FIG. 3 shows typical rebreathing curves of blood insoluble and blood soluble gases during a rebreathing test.

Figure 4:
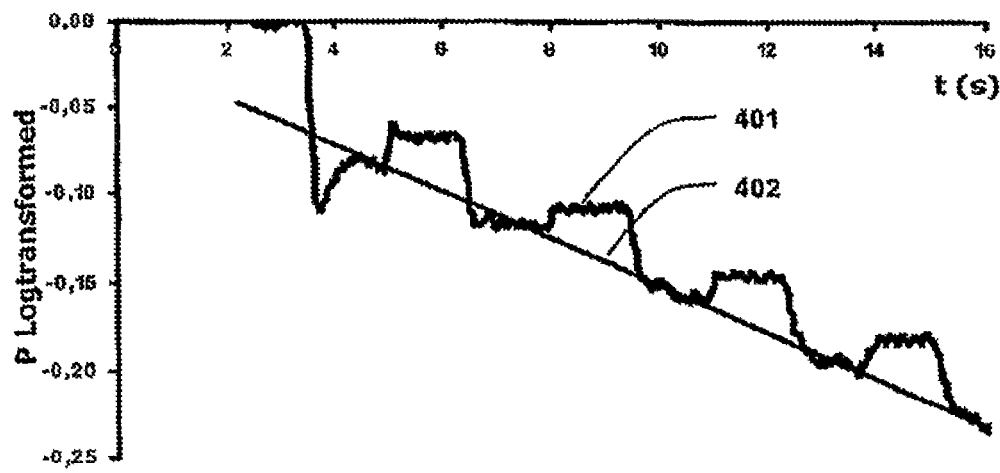
FIG. 4 is an example of a blood soluble gas rebreathing curve from a test as known in the art (see FIG. 3), normalized and logarithmically transformed.

The exponentially decaying partial pressure of the blood soluble gas can be represented by a rectilinear disappearance in a semi-logarithmic plot. FIG. 4 shows such a normalized and logarithmically transformed curve 401 of blood soluble gas during a rebreathing test. A regression line 402 is shown, the slope of which is used in the calculation of pulmonary blood flow as the disappearance rate (i.e. slope) is proportional to the pulmonary blood flow as also shown below.

Figure 5:
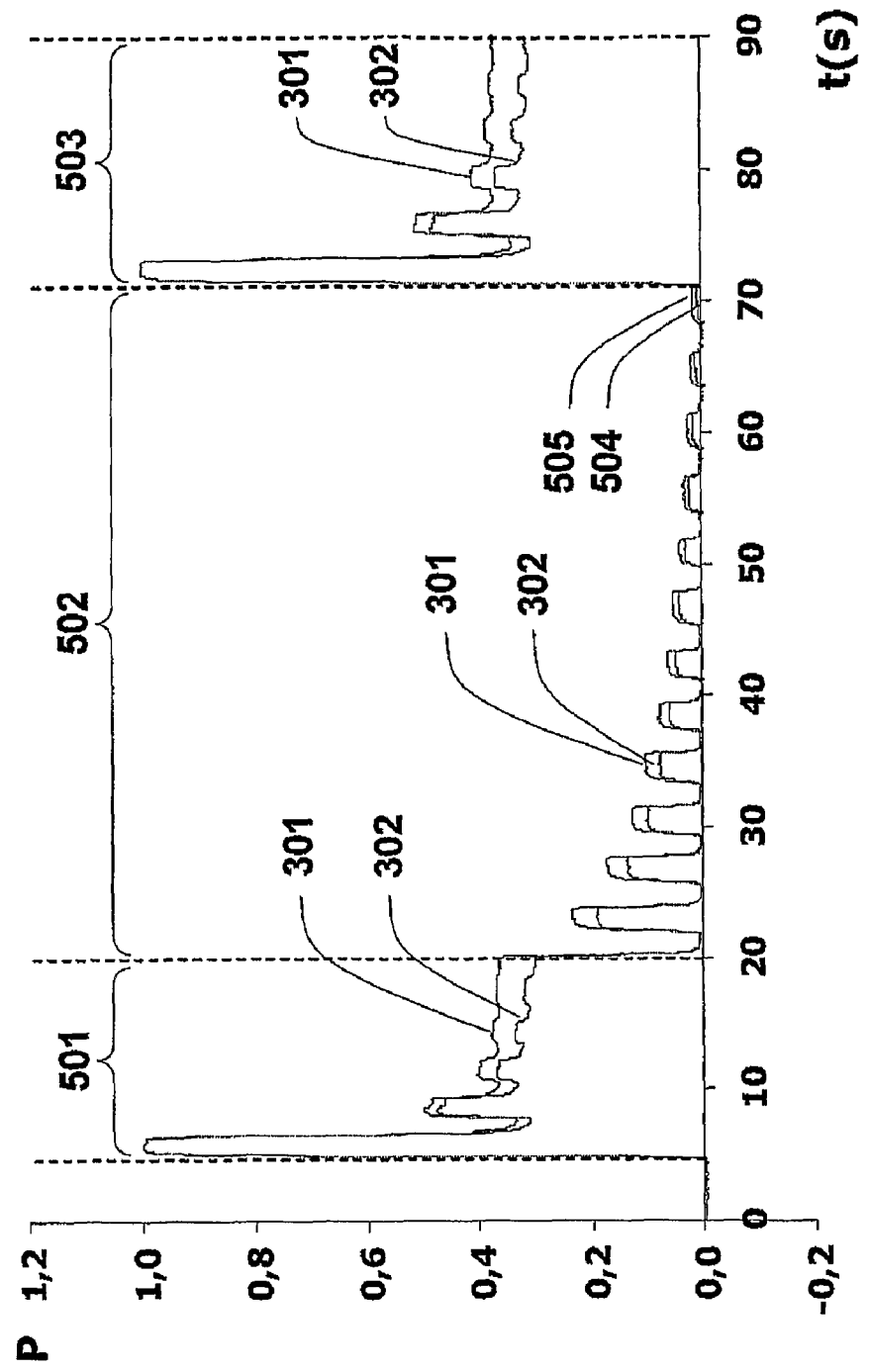
FIG. 5 is an example of a test sequence as used in conjunction with the disclosed invention, showing blood soluble and insoluble gas curves during a first rebreathing test, a subsequent washout period, and a second rebreathing test, respectively.

FIG. 5 is a typical example of a test sequence as used in conjunction with one embodiment of the disclosed invention, showing insoluble 301 and blood soluble 302 gas curves during a first rebreathing test 501, a subsequent washout period 502, and a second rebreathing test 503, respectively. The curves show the pressure over time as measured in the breathing assembly at the tip of the gas sample line 112. In the second rebreathing test 503 the assumption of a negligible partial pressure of the blood soluble gas in the mixed venous blood as used in a conventional inert gas rebreathing test (prior art) is invalid as seen by a non-zero end-tidal partial pressure 504 of the blood soluble gas immediately prior to the second test 503. Also the end-tidal partial pressure of the insoluble gas 505 prior to the second test 503 is non-zero.

The present invention then relates to a method to compensate for the effect of the recirculation on the determination of pulmonary blood flow in repeated tests by accounting for the known non-zero partial pressure of blood soluble gas in mixed venous blood. Furthermore, the present invention relates to a method to determine the mixed venous partial pressure non-invasively from ventilatory and inert gas concentration data in a number of breaths between the successive rebreathing tests. The invention comprises of a number of important parts:
A method to determine the partial pressure of the blood soluble compound in the mixed venous blood during washout of the blood soluble and the blood insoluble compounds between successive inert gas rebreathing tests.
A method to determine the pulmonary blood flow by the inert gas rebreathing method, taking into account the non-zero partial pressure of the blood soluble compound in the mixed venous blood.

One embodiment of the invention then applies the two methods according to the above on data obtained by a measuring device. This may in one embodiment involve an iterative approach to determine both the non-zero mixed venous partial pressure of the blood soluble gas and the pulmonary blood flow, which depend on each other.

The methods according to the one embodiment of the present invention to account for the non-zero mixed venous partial pressure of the blood soluble gas in the theory behind the respiration tests will be briefly outlined below. A more detailed and thorough derivation of the physical relations is given in the annexes 1-4.

Determination of the Pulmonary Blood Flow—Accounting for the Non-Zero Mixed Venous Partial Pressure of the Blood Soluble Gas The determination of the pulmonary blood flow by the inert gas rebreathing method will be briefly explained in the following, first as traditionally determined, then when the non-zero mixed venous partial pressure of the blood soluble gas is accounted for.

The mathematical model underlying the following expressions is derived by analyzing a simplified model of the lungs (see Annex 1, and set $P_{v,s}=0$).

The conventional method to determine the pulmonary blood flow (PBF) by the inert gas rebreathing method is to measure the slope of the washout curve of a blood soluble compound in a semi-logarithmic plot. The equation relating the PBF to this slope is:

$$PBF = -\beta \cdot \frac{V_S \cdot \frac{P_B^0}{P_B - P_{sat}} + V_t \cdot \alpha_t}{\alpha_b} \quad (1)$$

where
$V_S$=Combined lung-bag volume (STPD)
$P_B^0$=Standard barometric pressure (760 mmHg)
$P_B$=Barometric pressure (mmHg)
$P_{sat}$=Saturated water vapor pressure at 37° C. (47 mmHg)
$V_t$=Lung tissue volume
$\alpha_t$=Bunsen solubility coefficient for soluble gas in lung tissue [ml STPD/ml/atm at 37° C.]
$\alpha_b$ Bunsen solubility coefficient for soluble gas in blood [ml STPD/ml/atm at 37° C.]
STPD is standard nomenclature for Standard Temperature and Pressure, Dry. The last variable $\beta$ is the slope of the partial pressure curve of blood soluble gas in a semi-logarithmic plot after normalization:

$$\beta = \text{slope of } \ln\left(\frac{P_s(t) \cdot P_{rb,i}}{P_i(t) \cdot P_{rb,s}}\right) \quad (2)$$

where
$P_s(t)$=Partial pressure of blood soluble gas as a function of time
$P_i(t)$=Partial pressure of blood insoluble gas as a function of time
$P_{rb,i}$=Initial partial pressure of blood insoluble gas in the rebreathing bag
$P_{rb,s}$=Initial partial pressure of blood soluble gas in the rebreathing bag The total combined lung-bag volume $V_S$ is determined as:

$$V_s = V_{rb} + V_L \quad (3)$$

where
$V_{rb}$=Initial rebreathing bag volume
$V_L$=Lung (alveolar) volume (including serial dead space)

The lung volume $V_L$ and the lung tissue volume $V_t$ are determined using the equations in Annexes 2 and 3, setting $P_{v,s}=0$, $P_{A,i}=0$, and $P_{A,s}=0$.

As already mentioned, one of the basic assumptions of this model is that the partial pressure of the blood soluble gas in the mixed venous blood, $P_{v,s}$, is zero. An analysis of a model which allows non-zero values of $P_{v,s}$ (Annex 1 with all details) gives a modified expression for the relationship between PBF and the slope of the washout curve in a semi-logarithmic plot:

$$PBF = -\beta_c \cdot \frac{V_S \cdot \frac{P_B^0}{P_B - P_{sat}} + V_t \cdot \alpha_t}{\alpha_b} \quad (4)$$

where $$\beta_c = \text{slope of } \ln\left(\frac{(P_s(t) - P_{v,s}) \cdot P_{rb,i}}{P_i(t) \cdot P_{rb,s}}\right) \quad (5)$$

Hence, the PBF can, according to an embodiment of the invention, in effect be determined by setting off the measured curve by $-P_{v,s}$ followed by the conventional calculation method. It is easily seen that in case $P_{v,s}$ is zero, the new eqs. (4) and (5) can be reduced to the conventional eqs. (1) and (2) as should also be the case.

The lung volume $V_L$ and the lung tissue volume $V_t$ are again determined using the equations as outlined in Annexes 2 and 3, with all details.

Based on these derivations the PBF can be determined as a function of the measured physical parameters from the rebreathing test. However, as can be seen from equation (5), the PBF still depends on $P_{v,s}$ (the partial pressure of the blood soluble gas in the mixed venous blood) which still has to be determined. The determination of this parameter is outlined in the following.

Determination of the Non-Zero Mixed Venous Partial Pressure of the Blood Soluble Gas During Washout of the Blood Soluble and Insoluble Gases When a rebreathing test has been completed and the patient is breathing in an open breathing assembly, both the blood insoluble and the blood soluble gases are washed out from the body. The insoluble gas is washed out by inspiration of air without the gas and expiration of air with the partial pressure existing in the lungs.

The relationship between the end-tidal partial pressures of the insoluble gas in two succeeding breaths can be derived from different mass balance considerations. These are given in detail in Annex 4. The end-tidal partial pressures of the insoluble gas in breath number n+1 as a function of the previous breath number n yields:

$$P_{A,i}(n+1) = P_{A,i}(n) \cdot \frac{V_L(n) + V_D}{V_L(n+1) + V_E(n+1)} \quad (6)$$

where
$P_{A,i}$=End-tidal partial pressure of insoluble gas
$V_L$=Alveolar volume
$V_D$=Serial deadspace
$V_E$=Expired volume Since the gas is washed out at a rate proportional to its partial pressure in the lungs, the partial pressure is going down slowly in an exponential manner. If the lungs and rebreathing bag acted as a completely mixed compartment the washout would follow a mono-exponential curve. However, experimental washout curves typically require the summation of 2 to 3 exponentials with different rate constants in order to obtain an accurate representation of the experimental curve.

Using eq. (6) enables the creation of a theoretical washout curve for the blood insoluble gas from a single compartment model provided that the initial lung volume, $V_L(n)$ is determined, and the inspired and expired volumes ($V_I$ and $V_E$) are measured in each breath. As mentioned above the theoretical curve is expected to deviate from the experimental curve because the lungs do not behave as a single compartment unit. Thus, for each theoretical end-tidal partial pressure a correction factor can be chosen as:

$$CF(n) = \frac{P_{A,i}(n)_{theoretical}}{P_{A,i}(n)}. \quad (7)$$

The washout curve of the blood soluble compound is similar to the curve for the insoluble compound. However, the non-zero solubility of this compound implies an important difference. Initially, the rate of washout appears faster than the washout of the insoluble compound. The reason is that part of the soluble gas is transported away from the lungs by the blood perfusing the lungs. Later in the washout process the rate of washout of the soluble compound is slower than the washout of the insoluble compound. The reason for this is that the soluble gas previously deposited in the tissues during the rebreathing test and the initial part of the washout process is coming back to the lungs via the mixed venous blood. Hence, the effect of the transient deposition of the soluble gas in the tissues is to delay the washout of the soluble gas compared to the insoluble gas. A comparison of such two typical washout curves for the blood soluble and blood insoluble gases are shown in FIG. 5.

Analysis of the washout of a blood soluble compound from a single compartment lung model (Annex 4) from breath number n to breath number n+1 gives an expression for the relationship between the end-tidal partial pressure of the gas in breath n and breath n+1:

$$P_{A,s}(n+1) = \frac{P_{A,s}(n) \cdot (V_D + V_L(n) - P_B \cdot PBF \cdot \Delta t(n+1) \cdot \alpha_b \cdot 1/2) +}{V_L(n+1) + V_E(n+1) + P_B \cdot PBF \cdot \Delta t(n+1) \cdot \alpha_b \cdot 1/2} \quad (8)$$
$$+ \frac{P_B \cdot PBF \cdot \Delta t(n+1) \cdot \alpha_b \cdot P_{v,s}}{V_L(n+1) + V_E(n+1) + P_B \cdot PBF \cdot \Delta t(n+1) \cdot \alpha_b \cdot 1/2}$$

where
$P_{A,s}$=End-tidal partial pressure of the blood soluble gas
$\Delta t$=Duration of breath It is not possible to calculate the theoretical washout curve for the blood soluble gas in a similar way as for the insoluble gas (eq. (6)) because this equation depends on both PBF and $P_{v,s}$. However, it is possible to measure the washout curve experimentally and then obtain the theoretical curve by applying the correction factors (CF(n)) obtained from the blood insoluble gas (eq. (7)). This is because the influence of the multi-compartment behavior of the lungs on the blood insoluble gas is expected to be the same as the influence on the blood soluble compound.

Thus, from the experimentally recorded washout curve of the blood soluble compound a washout curve can be constructed, which, in theory, is described by eq. (9):

$$P_{A,s}(n)_{theoretical} = P_{A,s}(n) \cdot CF(n) \quad (9)$$

Based on the above established relationships the pulmonary blood flow can be determined. One embodiment of a system/device capable of doing so is sketched in FIG. 1 according to one aspect of the invention. One embodiment of a system/device for determining the PBF in a patient according to the invention comprises:

a breathing assembly which can switch (manually or automatically) between an open circuit mode and a closed rebreathing mode as illustrated in FIG. 1.

a gas dose facility enabling filling of the rebreathing bag to a known volume with a gas mixture containing both the blood soluble and the blood insoluble compound. Alternatively, the rebreathing bag can be prepared manually.

measuring means for continuous measurement of the partial pressures or concentrations of both the blood soluble and the blood insoluble gas during rebreathing.

measuring means for measuring end-tidal partial pressures or a continuous pressure curve of both the blood soluble and the blood insoluble gas during open-circuit breathing.

Optionally a measuring means for measuring flow or inspired and expired volumes in the open-circuit mode.

Consider a test sequence where the patient is performing first one rebreathing test followed by a washout period and then a second rebreathing test as the test sequence sketched in FIG. 5. The test periods do not have to be of equal length or of an equal number of breaths, which is a great advantage over other techniques known in the art. As earlier discussed the partial pressure of the blood soluble gas is not zero in the second rebreathing test due to the fact that part of the gas is still remaining from the previous test. The partial pressure curves of the two gases or at least the end-tidal partial pressures and pressures during the first inspirations from the rebreathing bag, and the inspired and expired volumes are measured during the entire test sequence.

Figure 6:
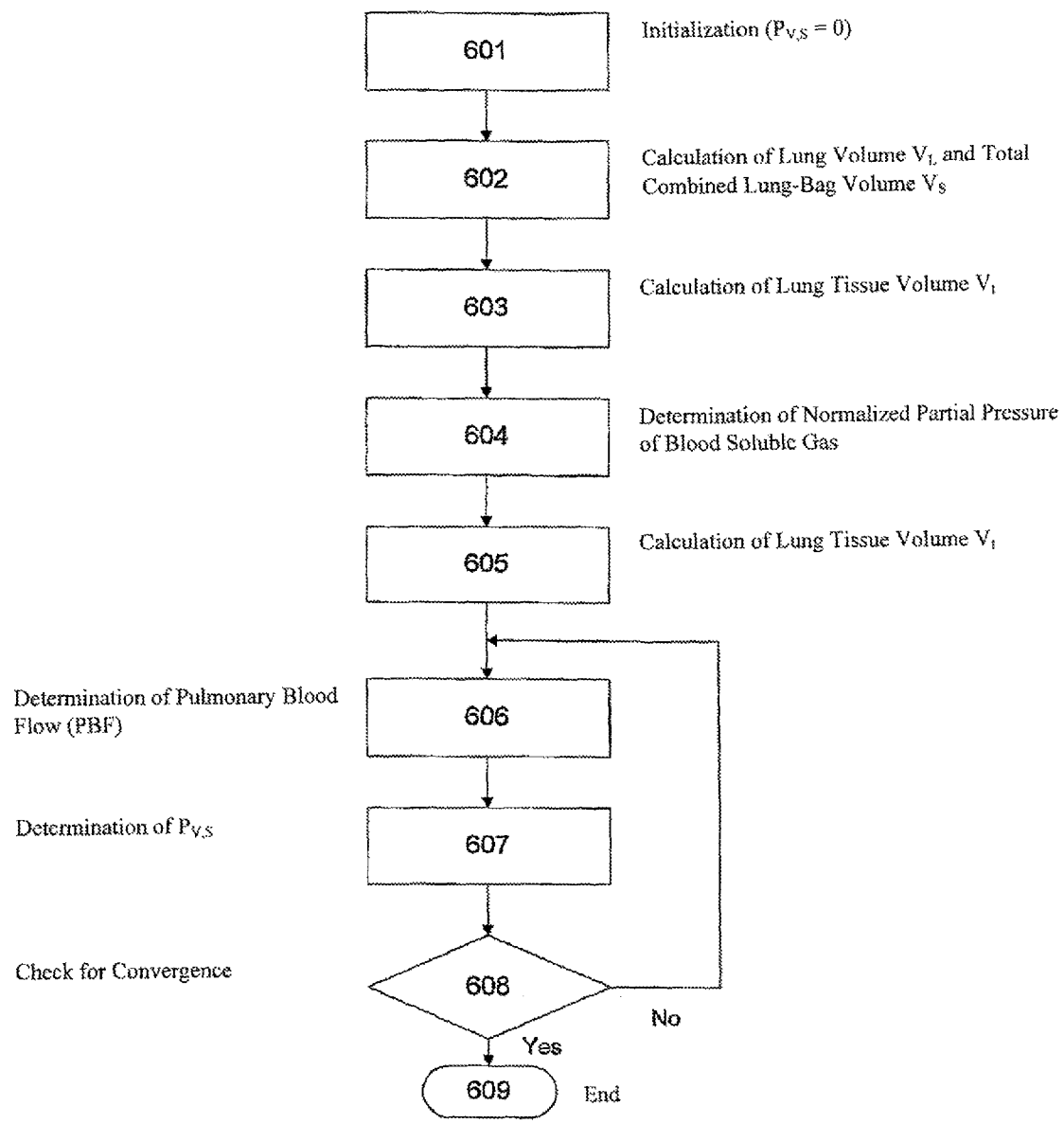
FIG. 6 is a flowchart showing an iterative calculation sequence that may be employed according to one embodiment of the invention.

The flowchart in FIG. 6 then illustrates an iterative calculation sequence that may be employed according to one embodiment of the present invention in order to determine the PBF in the second rebreathing test (where $P_{v,s}$ cannot be assumed to be zero). First, in step 601 $P_{v,s}$ is set to zero. The first step is to calculate the lung volume $V_L$, the total combined lung-bag volume $V_s$ and the lung tissue volume $V_t$ (for example by using the equations given in Annexes 2 and 3) in step 602 and 603, respectively. Since $P_{v,s}$ is not known the next step is to calculate a preliminary value of PBF in the second rebreathing test using eq. (4) and setting $P_{v,s}$ to zero. Using the preliminary value of PBF, $P_{v,s}$ in eq. (8) is then calculated by making a curve fit (for example a least squares curve fit) of the corrected washout curve of the blood soluble gas (eq. (9)) to the experimentally measured washout curve. This gives a $P_{v,s}$ value which is again used in eq. (4) to obtain a new estimate of PBF. This estimate is then used to calculate a new $P_{v,s}$ value by eq. (8). In step 604 the normalized partial pressures of blood soluble gas $P_s(t)$ are determined. Step 605 is a calculation of lung tissue volume $V_t$. Step 606 is a determination of pulmonary blood flow PBF. Step 607 is a determination of This iterative procedure is repeated, a number of times or until a sufficient convergence is obtained, i.e. there is no or little change in either $P_{v,s}$ or PBF between two successive iterations. Hence, step 608 is a check for convergence to determine if the iterative process should continue with step 606 or end with step 609.

Equations (6)-(9) are useful when neither the blood soluble nor the insoluble gas is completely washed out prior to a repeated rebreathing test. In case the insoluble gas is completely washed out prior to the repeated rebreathing test it is possible to establish a simpler relationship between the steady-state alveolar partial pressure of blood soluble gas, $P_{A,s}$, and the mixed venous partial pressure, $P_{v,s}$.

$$\frac{P_{A,s}}{P_B} \cdot \dot{V}_A = \alpha_b \cdot PBF \cdot (P_{v,s} - P_{A,s}) \quad (10)$$

where
$V_A$ is the alveolar ventilation determined from the ventilation at the mouth with correction for deadspace ventilation as known in the art.

Rearranging this equation leads to the expression for $P_{v,s}$:

$$P_{v,s} = P_{A,s} \cdot \left( \frac{\dot{V}_A}{\alpha_b \cdot P_B \cdot PBF} + 1 \right) \quad (11)$$

The flowchart in FIG. 6 is still applicable when using eq. (11) instead of eqs. (6)-(9) in that eq. (11) is applied in step 607.

It should be noted that the above-mentioned means of implementation illustrate rather than limit the invention, and that those skilled in the art will be able to suggest many alternative means of implementation without departing from the scope of the appended claims. Rather, the words used in the specification are words of description rather than limitation, and it is understood that various changes may be made without departing from the scope of the invention. The word 'comprising' does not exclude the presence of other elements or steps than those listed in a claim. The invention can be implemented by means of hardware and software comprising several distinct elements, and by means of a suitably programmed computer. In a device claim enumerating several means, several of these means can be implemented by one and the same item of hardware or software. The mere fact that certain measures are recited in mutually different dependent claims does not indicate that a combination of these measures cannot be used to advantage.

Annex 1—Analysis of a Simplified Model of the Lungs Assuming a Non-Zero Content of the Blood Soluble Gas in the Mixed Venous Blood Calculations are based on a single-alveolar lung model, which includes the following assumptions:

Complete and instantaneous mixing of all gases in the volume consisting of lung (alveolar) volume, dead spaces and bag volume.

Instantaneous equilibration of the blood soluble gas between the alveolar space and blood, and between alveolar space and tissue, respectively.

Constant pulmonary blood flow and constant volume of lung tissue.

Negligible or constant mixed venous partial pressure of blood soluble gas throughout the rebreathing period. For this assumption to be true, it is required that the test is terminated before recirculation occurs within the rebreathing period.

All mathematical expressions and illustrations throughout this document are made using partial pressures of the inert gases. Partial pressures can be replaced by fractional concentrations of dry gas or any other measure of gas concentration or pressure using appropriate conversion factors as known in the art.

Volumes are given at Standard Temperature and Pressure, Dry (STPD). Any other gas condition can be used using appropriate conversion factors as known in the art.

Assuming a constant partial pressure of the soluble gas in mixed venous blood, the mass balance equation for the soluble gas as a function of the time t during rebreathing can be written as:

$$PBF \cdot \alpha_b \cdot \frac{P_s(t) - P_{v,s}}{P_B^0} = -\frac{d\left(V_s(t) \cdot \frac{P_s(t)}{P_B - P_{sat}}\right)}{dt} - V_t \cdot \alpha_t \cdot \frac{d\left(\frac{P_s(t)}{P_B^0}\right)}{dt} \quad (A1.1)$$

where
PBF=Pulmonary blood flow [l/min]
$\alpha_b$=Bunsen solubility coefficient for the soluble gas in blood [ml(STPD)/ml per 1 atm of partial pressure at 37° C.]
$P_s(t)$=Partial pressure of soluble gas at time t [mmHg]
$P_{v,s}$=Mixed venous partial pressure of soluble gas [mmHg]
$P_B^0$=Standard pressure, 1 atm [760 mmHg]
$V_s(t)$=Total gas volume [liter STPD]
$P_B$=Barometric pressure [mmHg]
$P_{sat}$=Saturated water vapor pressure at 37° C. [mmHg]
$V_t$=Lung tissue volume [liter]
$\alpha_t$=Bunsen solubility coefficient for the soluble gas in lung tissue [ml(STPD)/ml per 1 atm of partial pressure at 37° C.]

The total gas volume is equal to:

$$V_S(t) = V_{rb} + V_L(t) \quad (A1.2)$$

in which
$V_{rb}$=Rebreathing bag volume [l STPD]
$V_L$=Lung (alveolar) volume (including serial dead space) [l STPD]

The partial pressure of the soluble gas can be expressed as a function of the fractional concentration of dry gas $F_s(t)$ (as measured by most gas analyzers) as:

$$P_s(t) = F_s(t) \cdot (P_B - P_{sat}) \quad (A1.3)$$

Assuming that the total volume is constant, $d(V_S(t))/dt=0$, eq. (A1.1) can be rewritten as:

$$\left(\frac{V_S}{P_B - P_{sat}} + V_t \cdot \frac{\alpha_t}{P_B^0}\right) \cdot \frac{dP_s(t)}{dt} + \quad (A1.4)$$

$$PBF \cdot \frac{\alpha_b}{P_B^0} \cdot P_s(t) + \left(-PBF \cdot \frac{\alpha_b}{P_B^0} \cdot P_{v,s}\right) = 0$$

By defining these constants, $$k_1 = \frac{V_s}{P_B - P_{sat}} + V_t \cdot \frac{\alpha_t}{P_B^0} \quad (A1.5)$$

$$k_2 = PBF \cdot \frac{\alpha_b}{P_B^0}$$

$$k_3 = -PBF \cdot \frac{\alpha_b}{P_B^0} \cdot P_{v,s}$$

eq. (A1.4) can be rewritten as:

$$k_1 \cdot \frac{dP_s(t)}{dt} + k_2 \cdot P_s(t) + k_3 = 0 \quad (A1.6)$$

The solution, $P_s(t)$, to this standard form first-order differential equation is an exponential function of this form:

$$P_s(t) = c_1 \cdot e^{c_2 \cdot t} + c_3 \quad (A1.7)$$

Thus, the soluble gas rebreathing curve is an exponentially decreasing curve. Using this general solution in the differential equation (eq. (A1.6)) leads to the following equation:

$$(k_1 \cdot c_1 \cdot c_2 + k_2 c_1) \cdot e^{c_2 \cdot t} + k_2 \cdot c_3 + k_3 = 0 \quad (A1.8)$$

Knowing that $c_2 < 0$, $c_3$ can be determined by letting $t \to \infty$:

$$c_3 = -\frac{k_3}{k_2} = P_{v,s} \quad (A1.9)$$

Setting t=0 yields:

$$c_1 \cdot (k_1 \cdot c_2 + k_2) + k_2 \cdot c_3 + k_3 = 0 \quad (A1.10)$$

Knowing that $c_3 = -k_3/k_2$ and $c_1 \neq 0$, $c_2$ can be determined as:

$$c_2 = -\frac{k_2}{k_1} = -PBF \cdot \frac{\alpha_b}{V_S \cdot \frac{P_B^0}{P_B - P_{sat}} + V_t \cdot \alpha_t} \quad (A1.11)$$

To determine the last constant $c_1$ it is necessary to look at the dilution of the blood soluble gas at the moment where the whole amount of soluble gas from the bag enters the alveolar space, $t=0^+$:

$$P_s(0^+) = c_1 + c_3 = \frac{P_{rb,s} \cdot V_{rb} + P_{A,s} \cdot (V_L + V_t \cdot \alpha_t)}{V_{rb} + V_L + V_t \cdot \alpha_t} \quad (A1.12)$$

where $P_{rb,s}$=Initial partial pressure of blood soluble gas in rebreathing bag
$P_{A,s}$=Alveolar (end-tidal) partial pressure of blood soluble gas prior to the start of rebreathing Hence, combining eqs. (A1.9) and (A1.12) yields:

$$c_1 = \frac{P_{rb,s} \cdot V_{rb} + P_{A,s} \cdot (V_L + V_t \cdot \alpha_t)}{V_{rb} + V_L + V_t \cdot \alpha_t} - P_{v,s} \quad (A1.13)$$

Combining eqs. (A1.7) and (A1.9), rearranging and applying a log-transform yields:

$$\ln(P_s(t) - P_{v,s}) = \ln(c_1 \cdot e^{c_2 \cdot t}) = \ln(c_1) + c_2 \cdot t \quad (A1.14)$$

Hence, $c_2$ is the slope of the rebreathing curve after being offset by and log-transformed:

$$c_2 = \beta_c \quad (A1.15)$$

Using this observation in eq. (A1.11) finally yields the expression for PBF:

$$PBF = -\beta_c \cdot \frac{V_S \cdot \frac{P_B^0}{P_B - P_{sat}} + V_t \cdot \alpha_t}{\alpha_b} \quad (A1.16)$$

$V_S$ in this equation is determined in accordance with Annex 2, and $V_t$ is determined in accordance with Annex 3.

Annex 2—Calculation of the Lung Volume During Rebreathing Using Blood Insoluble Gas During rebreathing the partial pressure of insoluble gas measured at the mouth decreases from the initial value in the rebreathing bag ($P_{rb,i}$) to a final equilibrium value ($P_{eq,i}$) practically obtained after a few breaths (FIG. 3). Since the volume of the rebreathing bag is known, the combined lung-bag volume ($V_S$) and the lung volume at the start of rebreathing ($V_L$) can be determined from the dilution of the insoluble gas. The total amount of insoluble gas can be expressed as:

$$V_{rb} \cdot P_{rb,i} + V_L \cdot P_{A,i} = (V_{rb} + V_L) \cdot P_{eq,i} \quad (A2.1)$$

where $V_{rb}$=Initial rebreathing bag volume
$V_L$=Lung volume at the start of rebreathing
$P_{rb,i}$=Initial partial pressure of insoluble gas in the rebreathing bag
$P_{eq,i}$=Equilibrium partial pressure of insoluble gas obtained after mixing (back extrapolated to the start of rebreathing)
$P_{A,i}$=Initial alveolar (end-tidal) partial pressure of insoluble gas in the alveolar space (due to incomplete washout)

This equation can be rearranged to yield an expression for the lung volume:

$$V_L = V_{rb} \cdot \frac{P_{rb,i} - P_{eq,i}}{P_{eq,i} - P_{A,i}} \quad (A2.2)$$

The combined lung-bag volume can be derived as:

$$V_S = V_{rb} + V_L = V_{rb} \cdot \frac{P_{rb,i} - P_{A,i}}{P_{eq,i} - P_{A,i}} \quad (A2.3)$$

where
$V_S$=Total, combined lung-bag volume

The above equations account for insoluble gas remaining in the lung volume from the previous test(s) at the start of rebreathing ($P_{A,i}$). If $P_{A,i}$ is set to zero, eqs. (A2.2) and (A2.3) reduce to the volume equations known in the art.

All volumes above must be expressed at the same conditions, e.g. standard temperature and pressure, dry (STPD) in the calculations but can be converted to e.g. body temperature and pressure, saturated (BTPS) as typically used to represent $V_L$ as a separate physiological parameter. Deadspaces on each side of the valve are not accounted for, but these can easily be incorporated e.g. by adding a volume term to either $V_{rb}$ or $V_L$ or both.

Annex 3—Calculation of the Lung Tissue Volume During Rebreathing Using Blood Soluble Gas The lung tissue volume $V_t$ is determined by rearrangement of eq. (A1.12):

$$P_s(0^+) \cdot (V_{rb} + V_L) + P_s(0^+) \cdot V_t \cdot \alpha_t - P_{A,s} \cdot V_t \cdot \alpha_t = P_{rb,s} \cdot V_{rb} + P_{A,s} \cdot V_L \quad (A3.1)$$

Reduction yields:

$$V_t = \frac{1}{\alpha_t \cdot (P_s(0^+) - P_{A,s})} \cdot \{P_{rb,s} \cdot V_{rb} + P_{A,s} \cdot V_L - P_s(0^+) \cdot (V_{rb} + V_L)\} \quad (A3.2)$$

By setting $P_{A,s}$ equal to zero, the conventional equation for $V_t$ is obtained:

$$V_t = \frac{1}{\alpha_t \cdot P_s(0^+)} \cdot \{P_{rb,s} \cdot V_{rb} - P_s(0^+) \cdot (V_{rb} + V_L)\} \quad (A3.3)$$

Annex 4—Analysis of the Washout of a Blood Soluble Compound from a Single Compartment Lung Model Mass Balance Equation for Blood Soluble Gas During washout (i.e. in the period following a rebreathing test where there is no blood soluble gas in inspired gas) mass balance for the blood soluble gas in the alveolar space in breath number n+1 can be expressed:

$$\frac{P_{A,s}(n+1)}{P_B} \cdot V_L(n+1) - \frac{P_{A,s}(n)}{P_B} \cdot V_L(n) = \\ \frac{P_{A,s}(n)}{P_B} \cdot V_D - \frac{P_{A,s}(n+1)}{P_B} \cdot V_E(n+1) + \\ PBF \cdot \alpha_b \cdot \Delta t(n+1) \cdot \left\{ P_{v,s} - \frac{P_{A,s}(n+1) + P_{A,s}(n)}{2} \right\} \quad (A4.1)$$

where
$P_{A,s}$=Alveolar (end-tidal) partial pressure of blood soluble gas
$V_L$=Alveolar (lung) volume
$P_B$=Barometric pressure
$V_E$=Expired volume
PBF=Pulmonary blood flow
$\alpha_b$=Solubility coefficient of blood soluble gas
$\Delta t$=Duration of breath
$P_{v,s}$=Mixed venous partial pressure of blood soluble gas
$V_D$=Serial deadspace Rearrangement of eq. (A4.1) gives the relationship between $P_{A,s}$ in two consecutive breaths:

$$P_{A,s}(n+1) \cdot \{V_L(n+1)+V_E(n+1)+P_B \cdot PBF \cdot \Delta t(n+1) \cdot \alpha_b \cdot \tfrac{1}{2}\} = P_{A,s}(n) \cdot \{V_D+V_L(n)-P_B \cdot PBF \cdot \Delta t(n+1) \cdot \alpha_b \cdot \tfrac{1}{2}\}+P_B \cdot PBF \cdot \Delta t(n+1) \cdot \alpha_b \cdot P_{v,s} \quad (A4.2)$$

Further rearrangement leads to an expression for $P_{v,s}$:

$$P_{v,s} = \frac{P_{A,s}(n+1)}{P_B \cdot PBF \cdot \alpha_b \cdot \Delta t(n+1)} \cdot \{V_L(n+1) + V_E(n+1)\} - \\ \frac{P_{A,s}(n)}{P_B \cdot PBF \cdot \alpha_b \Delta t(n+1)} \cdot \{V_L(n) + V_D\} + \frac{P_{A,s}(n+1) + P_{A,s}(n)}{2} \quad (A4.3)$$

Total Mass Balance Equation

To derive the alveolar volume in breath number n+1 from the volume in breath n for use in eq. (A4.3), the mass balance for all gases in the alveolar space in breath n+1 is established:

$$V_L(n+1)=V_L(n)+V_I(n+1)-V_E(n+1) \quad (A4.4)$$

where
$V_I$=Inspired volume

Mass Balance Equation for Insoluble Gas

During washout (i.e. in the period following a rebreathing test where there is no insoluble gas in inspired gas) mass balance for the insoluble gas in the alveolar space in breath number n+1 can be expressed:

$$\frac{P_{A,i}(n+1)}{P_B} \cdot V_L(n+1) - \frac{P_{A,i}(n)}{P_B} \cdot V_L(n) = \\ \frac{P_{A,i}(n)}{P_B} \cdot V_D - \frac{P_{A,i}(n+1)}{P_B} \cdot V_E(n+1) \quad (A4.5)$$

where
$P_{A,i}$=Alveolar (end-tidal) partial pressure of insoluble gas

Rearrangement of eq. (A4.5) yields:

$$P_{A,i}(n+1) \cdot \{V_L(n+1)+V_E(n+1)\}=P_{A,i}(n) \cdot \{V_D+V_L(n)\} \quad (A4.6)$$

Further rearrangement leads to:

$$P_{A,i}(n+1) = P_{A,i}(n) \cdot \frac{V_D + V_L(n)}{V_L(n+1) + V_E(n+1)} \quad (A4.7)$$

The invention claimed is:

1. A method to compensate for a non-zero mixed venous partial pressure of inert blood soluble gas when determining physical parameter(s) of a patient in successive inert gas rebreathing tests, said method comprising the steps of:
obtaining a partial pressure of said inert blood soluble gas inhaled and/or exhaled by said patient during a period prior to one of said successive inert gas rebreathing tests;
obtaining a partial pressure of said inert blood soluble gas inhaled and/or exhaled by said patient in said one of said successive inert gas rebreathing tests;

determining said physical parameter(s) and using a processor in an iterative procedure including the steps of:

extracting a first parameter using said obtained partial pressure of said inert blood soluble gas inhaled and/or exhaled by said patient in said one of said successive inert gas rebreathing tests;

extracting a second parameter using said first parameter and said obtained partial pressure of said inert blood soluble gas inhaled and/or exhaled by said patient during said period prior to said one of said successive inert gas rebreathing tests;

re-extracting said first parameter using said second parameter and said obtained partial pressure of said inert blood soluble gas inhaled and/or exhaled by said patient in said one of said successive inert gas rebreathing tests.

2. A method according to claim 1 wherein the iterative procedure of said method further comprises the steps of:

repeating the steps of extracting said second parameter and re-extracting said first parameter a number of times, such that said re-extracted first parameter is used in said step of extracting said second parameter.

3. A method according to claim 1, wherein said steps of obtaining the partial pressure of said inert blood soluble gas include the step of obtaining concentrations of said inert blood soluble gas.

4. A method according to claim 1, wherein said first parameter includes a cardiac parameter comprising a cardiac output of said patient.

5. A method according to claim 1, wherein said second parameter includes the mixed venous partial pressure of said inert blood soluble gas.

6. A method according to claim 1, wherein said method further comprises the steps of:

obtaining a partial pressure of an inert blood insoluble gas inhaled and/or exhaled by said patient;

using said partial pressure of said inert blood insoluble gas when determining said physical parameter(s), said first parameter, and/or said second parameter.

7. A method according to claim 6 wherein said step of obtaining the partial pressure of said inert blood insoluble gas includes the step of obtaining concentrations of said inert blood insoluble gas.

8. A method according to claim 6, wherein said step of determining said physical parameter(s) is based on mass conservation of said inert blood soluble gas and/or said inert blood insoluble gas.

9. A method according to claim 1, wherein said method further comprises the step of obtaining a gas flow inhaled and/or exhaled by said patient.

10. A central processing unit including a computer-readable medium having stored therein instructions for causing the central processing unit to execute the method according to claim 1.

11. A system adapted to compensate for a non-zero mixed venous partial pressure of inert blood soluble gas when determining physical parameter(s) of a patient in successive inert gas rebreathing tests, said system comprising:

at least one gas analyzer for obtaining a partial pressure of said inert blood soluble gas inhaled and/or exhaled by said patient during a period prior to one of said successive inert gas rebreathing tests;

at least one gas analyzer for obtaining a partial pressure of said inert blood soluble gas inhaled and/or exhaled by said patient in said one of said successive inert gas rebreathing tests;

processing means for determining said physical parameter(s) in an iterative process, comprising processing means for:

extracting a first parameter using said obtained partial pressure of said inert blood soluble gas inhaled and/or exhaled by said patient in said one of said successive inert gas rebreathing tests;

extracting a second parameter using said first, parameter and said obtained partial pressure of said inert blood soluble gas inhaled and/or exhaled by said patient during said period prior to said one of said successive inert gas rebreathing tests;

re-extracting said first parameter using said second parameter and said obtained partial pressure of said inert blood soluble gas inhaled and/or exhaled by said patient in said one of said successive inert gas rebreathing tests.

12. A system according to claim 11 wherein said system further comprises:

processing means for the iterative process which further comprises the steps of repeating the steps of extracting said second parameter and re-extracting said first parameter a number of times, such that said re-extracted first parameter is used in said step of extracting said second parameter.

13. A system according to claim 11, wherein said gas analyzers for obtaining the partial pressure of said inert blood soluble gas comprise means for obtaining concentrations of said inert blood soluble gas.

14. A system according to claim 11, wherein said first parameter comprises a cardiac parameter comprising a cardiac output of said patient.

15. A system according to claim 11, wherein said second parameter comprises the mixed venous partial pressure of said inert blood soluble gas.

16. A system according to claim 11, wherein said system further comprises:

at least one gas analyzer for obtaining a partial pressure of an inert blood insoluble gas inhaled and/or exhaled by said patient;

processing means for using said partial pressure of said inert blood insoluble gas when determining said physical parameter(s).

17. A system according to claim 16 wherein said at least one gas analyzer for obtaining the partial pressure of an inert blood insoluble gas includes means for obtaining concentrations of said inert blood insoluble gas.

18. A system according to claim 16, wherein said processing means for determining said physical parameter(s) uses mass conservation of said inert blood soluble gas and/or said inert blood insoluble gas.

19. A system according to claim 11, wherein said system further comprises a flowmeter for obtaining a gas flow inhaled and/or exhaled by said patient.

\* \* \* \* \*